(12) United States Patent
Pal et al.

(10) Patent No.: US 8,956,862 B2
(45) Date of Patent: Feb. 17, 2015

(54) METHODS OF PREPARING MESENCHYMAL STEM CELLS, COMPOSITIONS AND KIT THEREOF

(75) Inventors: Rakhi Pal, Karnataka (IN); Pawan Kumar Gupta, Karnataka (IN); Prasanna Kumar Kemburu, Karnataka (IN); Jyothi Prasanna, Karnataka (IN); Satish Totey, Karnataka (IN); Raviraja Neelavar Seetharam, Karnataka (IN); Umesh Baikunje Golithadka, Karnataka (IN); Anish Sen Majumdar, Karnataka (IN)

(73) Assignee: Stempeutics Research Pvt. Ltd., Bangalore (IN)

( * ) Notice: Subject to any disclaimer, the term of this patent is extended or adjusted under 35 U.S.C. 154(b) by 230 days.

(21) Appl. No.: 13/062,189

(22) PCT Filed: Nov. 25, 2010

(86) PCT No.: PCT/IB2010/055424
§ 371 (c)(1),
(2), (4) Date: Mar. 3, 2011

(87) PCT Pub. No.: WO2011/064733
PCT Pub. Date: Jun. 3, 2011

(65) Prior Publication Data
US 2011/0229965 A1    Sep. 22, 2011

(30) Foreign Application Priority Data
Nov. 27, 2009   (IN) .......................... 2932/CHE/2009

(51) Int. Cl.
*C12N 5/077* (2010.01)
*C12N 5/0775* (2010.01)
(52) U.S. Cl.
CPC .................................. *C12N 5/0663* (2013.01)
USPC ....................................................... 435/325

(58) Field of Classification Search
None
See application file for complete search history.

(56) References Cited

U.S. PATENT DOCUMENTS

| 5,827,735 A * | 10/1998 | Young et al. .................. 435/325 |
| 6,355,239 B1 * | 3/2002 | Bruder et al. ................. 424/93.1 |
| 2010/0047213 A1 * | 2/2010 | Zeitlin et al. ................. 424/93.7 |
| 2011/0150845 A1 * | 6/2011 | Parekkadan et al. ......... 424/93.7 |
| 2011/0262402 A1 * | 10/2011 | Kuroda et al. ............... 424/93.7 |

FOREIGN PATENT DOCUMENTS

| WO | WO 2007/024441 A2 | 3/2007 | |
| WO | WO 2008/129563 | * 10/2008 | ............... C12N 5/00 |

OTHER PUBLICATIONS

Amado et al., "Cardiac repair with intramyocardial injection of allogeneic mesenchymal stem cells after myocardial infarction", *Proc. Natl. Acad. Sci. USA.*, 102(32):11474-11479 (2005).
Kotobuki et al., "Cultured autologous human cells for hard tissue regeneration: preparation and characterization of mesenchymal stem cells from bone marrow", *Artif. Organs.*, 28(1):33-39 (2004).
Kotobuki et al., "Viability and osteogenic potential of cryopreserved human bone marrow-derived mesenchymal cells", *Tissue Eng.*, 11(5-6):663-673 (2005).
Wexler et al., "Adult bone marrow is a rich source of human mesenchymal 'stem' cells but umbilical cord and mobilized adult blood are not", *Br. J. Haematol.*, 121(2):368-374 (2003).
International Search Report (ISR) from PCT/IB2010/055424.

* cited by examiner

*Primary Examiner* — Allison Fox
*Assistant Examiner* — Yvonne Pyla
(74) *Attorney, Agent, or Firm* — DLA Piper LLP (US)

(57) ABSTRACT

The present invention discloses a method of isolation, pooling and further culturing of Mesenchymal Stem cells (MSC) for clinical application. Present invention also discloses the method of establishing Master Cell bank, followed by Working Cell Bank from which the final therapeutic composition referred to as Investigational Product/Investigational Medicinal Product comprising of allogenic bone marrow-derived MSC is formulated for clinical applications.

6 Claims, 2 Drawing Sheets

METHODS OF PREPARING MESENCHYMAL STEM CELLS, COMPOSITIONS AND KIT THEREOF

CROSS REFERENCE TO RELATED APPLICATIONS

This application is a 35 USC §371 National Stage application of International Application No. PCT/IB2010/055424 filed Nov. 25, 2010, which claims the benefit under 35 USC §119(a) to India Patent Application No. 2932/CHE/2009 filed Nov. 27, 2009. The disclosure of each of the prior applications is considered part of and is incorporated by reference in the disclosure of this application.

TECHNICAL FIELD

The present disclosure relates to stem cell processing and method of arriving at a stem cell based composition for clinical application. Specifically, it relates to method of processing aspirated bone marrow to isolate mesenchymal stem cells (MSC) and their large scale culturing/expansion for further clinical application.

BACKGROUND

Human mesenchymal stem cells (hMSC) are present as a rare population of cells in bone marrow, representing 0.001 to 0.01% of the nucleated cells, but they can rapidly grow and expand in culture without losing their stemness. The hMSC, with their attributes of (1) ease of isolation, (2) high expansion potential, (3) genetic stability, (4) reproducible attributes from isolate to isolate, (5) reproducible characteristics, (6) compatibility with tissue engineering principles, have the potential to enhance repair in many damaged tissues.

MSCs and MSC-like cells have now been isolated from various tissues other than the bone marrow which includes adipose tissue, amniotic fluid, periostium and foetal tissues, and show phenotypic heterogeneity. Phenotypically, MSCs express a number of markers, none of which, unfortunately, are specific to MSCs.

Mesenchymal stem cells obtained from human bone marrow (hBMSCs) have been widely studied because of their relative easy access and differentiation potential to the osteogenic, adipogenic and chondrogenic lineages, and other kind of tissues or cells, including hepatocytes, cardiomyocytes and neurons. Their multipotentiality and self-renewal has increased the attention to this stem cell as a self-renewing cell source with applications in regenerative medicine. In addition, their isolation based on the adherence to the culture substrates constitutes a straightforward strategy for elimination of non-mensenchymal lineages, reducing the dependency on complex cell isolation methods which rely on the expression of specific surface markers.

The limitation with bone marrow derived MSC is its small quantity but for clinical application large quantity of MSCs are required. The present disclosure provides method of processing bone marrow derived MSC and their further large scale expansion for clinical application.

STATEMENT OF THE DISCLOSURE

Accordingly, the present disclosure relates to a method of preparing a Master Cell Bank composition comprising Mesenchymal stem cells, Fetal Bovine Serum (FBS) and Dimethyl Sulphoxide (DMSO), said method comprising acts of—a) obtaining and diluting bone marrow cells in culture media and centrifuging the diluted cells to obtain a first pellet and re-diluting the first pellet with the culture media, b) adding density gradient solution to the re-diluted pellet and centrifuging to obtain a buffy layer at interface, c) re-adding equal volume of the culture media to the buffy layer and centrifuging to obtain a second pellet, followed by suspending the second pellet in the culture media and incubating to achieve about 80% to about 85% confluency, d) aspirating the culture media and washing the confluent cells with Dulbecco's Phosphate Buffered Saline (DPBS), thereafter treating the cells with 0.25% trypsin and re-incubating the treated cells, e) neutralizing the re-incubated cells with neutralization media and re-centrifuging the cells to obtain a third pellet, followed by suspending the third pellet in the culture media and freezing the cells with freezing media comprising about 85% to 95% FBS and about 5% to 15% DMSO and f) trypsinization of the frozen cells and resuspending the trypsinized cells in the freezing media to obtain the Master Cell Bank composition; a method of preparing a Working Cell Bank composition comprising Mesenchymal stem cells, Fetal Bovine Serum (FBS) and Dimethyl Sulphoxide (DMSO), said method comprising acts of—a) preparing a Master Cell Bank composition as above from bone marrow cells obtained from different-donors, b) obtaining cell pellet from the composition, followed by suspending the cell pellet in culture media and pooling the cells in equal proportion to obtain an aggregate of cells, c) culturing the aggregate of cells with the culture media, thereafter incubating to achieve about 80% to 85% confluency and re-performing above step (d), d) neutralizing the re-incubated cells with the culture media, followed by centrifuging the cells to obtain a second pellet and suspending the second pellet in the culture media to obtain cultured cells, and e) re-centrifuging the cultured cells and freezing the cell pellet with freezing media comprising about 85 to 95% FBS and about 5 to 15% DMSO to obtain the Working Cell Bank composition; a method of preparing a composition comprising Mesenchymal stem cells, PLASMA-LYTE A® (Multiple Electrolytes Injection, Type I USP), Human Serum Albumin (HSA), Dimethyl Sulphoxide (DMSO), optionally along with pharmaceutically acceptable additives, said method comprising acts of—a) preparing a Working Cell Bank composition as above, b) obtaining mesenchymal stem cells from the composition, followed by culturing the cells with culture media and incubating to achieve about 80% to 85% confluency, and re-performing above step (d), c) neutralizing the re-incubated cells with the culture media and thereafter centrifuging the cells to obtain a cell pellet, washing the cell pellet in DPBS followed by re-centrifuging to obtain a second cell pellet, d) suspending the second cell pellet in the complete media and culturing the cells, followed by incubating the cultured cells and adding the complete media to the incubated cells to achieve about 80% to 85% confluency, e) trypsinization of the confluent cells and re-washing the cells with the DPBS followed by treating the re-washed cells with 0.25% trypsin and incubating the treated cells followed by neutralizing the incubated cells with the complete media, f) centrifuging the neutralized cells and washing the centrifuged cells with the DPBS followed by re-centrifuging to obtain a third pellet and g) freezing the third pellet with the PLASMA-LYTE A®, the DMSO and the Human Serum Albumin and optionally adding pharmaceutically acceptable additive to obtain the composition; a composition comprising Mesenchymal Stem Cells, Human Serum Albumin (HSA), PLASMA-LYTE A®, and Dimethyl Sulphoxide (DMSO), optionally along with pharmaceutically acceptable additives; a Master Cell or Working Cell Bank Composition comprising Mesenchymal Stem cells, Fetal Bovine Serum (FBS) and Dimethyl Sulphoxide (DMSO); and a Kit comprising above compositions and an instructions manual.

BRIEF DESCRIPTION OF ACCOMPANYING FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure where:

FIG. 4 shows a photograph of Investigation product (IP) at passage 5 (Magnification 100×) showing characteristic morphology, spindle shaped and fibroblast like.

DETAILED DESCRIPTION OF THE INVENTION

Figure 1:
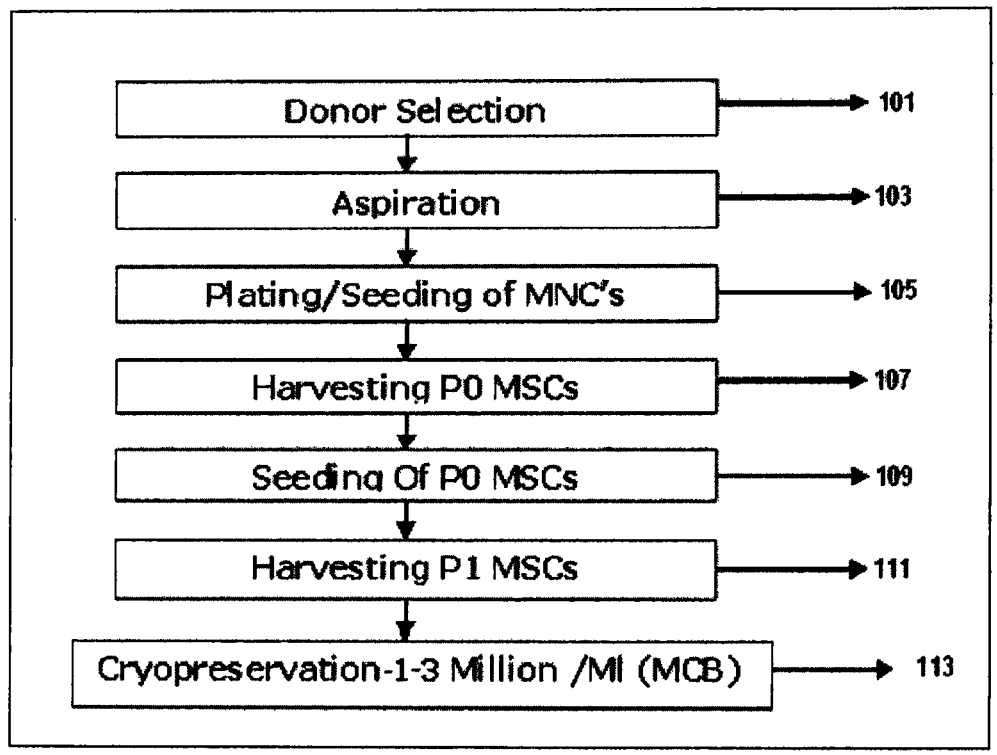
FIG. 1 shows a flow chart depicting steps involved in arriving at Master Cell Bank (MCB).

The present disclosure relates to a method of preparing a Master Cell Bank composition comprising Mesenchymal stem cells, Fetal Bovine Serum (FBS) and Dimethyl Sulphoxide (DMSO), said method comprising acts of:
  a. obtaining and diluting bone marrow cells in culture media and centrifuging the diluted cells to obtain a first pellet and re-diluting the first pellet with the culture media;
  b. adding density gradient solution to the re-diluted pellet and centrifuging to obtain a buffy layer at interface;
  c. re-adding equal volume of the culture media to the buffy layer and centrifuging to obtain a second pellet, followed by suspending the second pellet in the culture media and incubating to achieve about 80% to about 85% confluency;
  d. aspirating the culture media and washing the confluent cells with Dulbecco's Phosphate Buffered Saline (DPBS), thereafter treating the cells with 0.25% trypsin and re-incubating the treated cells;
  e. neutralizing the re-incubated cells with neutralization media and re-centrifuging the cells to obtain a third pellet, followed by suspending the third pellet in the culture media and freezing the cells with freezing media comprising about 85% to 95% FBS and about 5% to 15% DMSO; and
  f. trypsinization of the frozen cells and resuspending the trypsinized cells in the freezing media to obtain the Master Cell Bank composition.

In an embodiment of the present disclosure, the incubation is carried out in a 5% $CO_2$ incubator at a temperature of about 37° C.; the confluency is obtained by replenishing the culture media after about 7 days to 8 days; the neutralization media comprising Dulbecco's Modified Eagle Medium-KnockOut [DMEM KO], about 10% Fetal Bovine Serum [FBS] and about 0.5% Pen-Strep; and the re-incubating is done in a 37° C. incubator for about 2 minutes to 3 minutes.

The present disclosure relates to a method of preparing a Working Cell Bank composition comprising Mesenchymal stem cells, Fetal Bovine Serum (FBS) and Dimethyl Sulphoxide (DMSO), said method comprising acts of:
  a. preparing a Master Cell Bank composition as above from bone marrow cells obtained from different-donors;
  b. obtaining cell pellet from the composition, followed by suspending the cell pellet in culture media and pooling the cells in equal proportion to obtain an aggregate of cells;
  c. culturing the aggregate of cells with the culture media, thereafter incubating to achieve about 80% to 85% confluency and re-performing above step (d);
  d. neutralizing the re-incubated cells with the culture media, followed by centrifuging the cells to obtain a second pellet and suspending the second pellet in the culture media to obtain cultured cells; and
  e. re-centrifuging the cultured cells and freezing the cell pellet with freezing media comprising about 85 to 95% FBS and about 5 to 15% DMSO to obtain the Working Cell Bank composition.

In an embodiment of the present disclosure, the Master Cell Bank composition comprises Mesenchymal stem cells ranging from about 1 million cells to 3 million cells, Fetal Bovine Serum (FBS) ranging from about 85% to 95% and Dimethyl Sulphoxide (DMSO) ranging from about 5% to 15%.

In another embodiment of the present disclosure, the obtaining of the cell pellet is by thawing stem cells, neutralizing freezing media with complete media and centrifuging at about 1200 rpm to 1500 rpm for duration of about 10 to 20 minutes to obtain cell pellet. The present disclosure relates to a method of preparing a composition comprising Mesenchymal stem cells, PLASMA-LYTE A®, Human Serum Albumin (HSA), Dimethyl Sulphoxide (DMSO), optionally along with pharmaceutically acceptable additives, said method comprising acts of:
  a. preparing a Working Cell Bank composition as above,
  b. obtaining mesenchymal stem cells from the composition, followed by culturing the cells with culture media and incubating to achieve about 80% to 85% confluency, and re-performing above step (d);
  c. neutralizing the re-incubated cells with the culture media and thereafter centrifuging the cells to obtain a cell pellet; washing the cell pellet in DPBS followed by re-centrifuging to obtain a second cell pellet;
  d. suspending the second cell pellet in the complete media and culturing the cells, followed by incubating the cultured cells and adding the complete media to the incubated cells to achieve about 80% to 85% confluency;
  e. trypsinization of the confluent cells and re-washing the cells with the DPBS; followed by treating the re-washed cells with 0.25% trypsin and incubating the treated cells followed by neutralizing the incubated cells with the complete media;
  f. centrifuging the neutralized cells and washing the centrifuged cells with the DPBS followed by re-centrifuging to obtain a third pellet; and
  g. freezing the third pellet with the PLASMA-LYTE A®, the DMSO and the Human Serum Albumin; and optionally adding pharmaceutically acceptable additive to obtain the composition.

In an embodiment of the present disclosure, the Working Cell Bank composition having Mesenchymal stem cells ranging from about 1 million cells to 3 million cells, Fetal Bovine Serum (FBS) ranging from about 85% to 95% and Dimethyl Sulphoxide (DMSO) ranging from about 5% to 15%.

In another embodiment of the present disclosure, the centrifuging is carried out at about 1200 rpm to 1500 rpm, at temperature ranging from about 20° C. to 25° C. for time duration ranging from about 10 minutes to 20 minutes.

In yet another embodiment of the present disclosure, the incubating is done in a 5% $CO_2$ incubator at a temperature of about 37° C.; and wherein the confluency is obtained by replenishing the culture media after about 7 days to 8 days; and wherein the re-incubating is done in a 37° C. incubator for about 2 minutes to 3 minutes.

In still another embodiment of the present disclosure, the culture media comprises Dulbecco's Modified Eagle Medium-KnockOut [DMEM-KO] at a concentration ranging from about 85% to 95%, Fetal Bovine Serum [FBS] at a concentration ranging from about 5% to 15%, Glutamine at a concentration ranging from about 0.5% to 2%; Pen-Strep at a concentration ranging from about 0.1% to 1%, and basic Fibroblast growth Factor [bFGF] at a concentration ranging from about 0.5 ng/ml to 5 ng/ml.

The present disclosure relates to a composition comprising Mesenchymal Stem Cells, Human Serum Albumin (HSA), PLASMA-LYTE A®, and Dimethyl Sulphoxide (DMSO), optionally along with pharmaceutically acceptable additives.

The present disclosure relates to a Master Cell or Working Cell Bank Composition comprising Mesenchymal Stem cells, Fetal Bovine Serum (FBS) and Dimethyl Sulphoxide (DMSO).

In an embodiment of the present disclosure, the Mesenchymal Stem Cells having concentration ranging from about 25 million to 200 million cells; the Human Serum Albumin having concentration ranging from about 1% to 6%; the PLASMA-LYTE A®, having concentration ranging from about 80% to 90%; and the Dimethyl Sulfoxide having concentration ranging from about 5% to 10% in each cryo-preserved vial.

In another embodiment of the present disclosure, the Mesenchymal Stem Cells having concentration ranging from about 1 million to 3 million cells; the Fetal Bovine Serum having concentration ranging from about 85% to 95%; and the Dimethyl Sulfoxide having concentration ranging from about 5% to about 15% in each cryo-preserved vial. In yet another embodiment of the present disclosure, the pharmaceutically acceptable additive is PLASMA-LYTE A®.

The present disclosure relates to a kit comprising above compositions, and an instructions manual.

The present disclosure presents a method of isolation, pooling and large scale expansion for therapeutic application of bone marrow derived MSCs. It also discloses essential method of preserving/storing freshly harvested Mesenchymal Stem cells (MSCs/frozen-thawed MSCs for/before transplantation in optimal conditions so as to maintain their viability and multipotentiality for specified durations. In addition, the present disclosure also relates to a composition comprising Mesenchymal Stem cells (MSCs), Human Serum Albumin, PLASMA-LYTE A® and Dimethyl sulfoxide (DMSO) with pharmaceutically acceptable excipients for clinical applications. The present disclosure also relates to a method of obtaining the said composition. The method further involves establishing Master cell bank from aspirated bone marrow followed by preparing working cell bank and finally arriving at the composition of Investigational Medicinal Product.

In an embodiment of the present disclosure, as used herein the terms "Investigational Medicinal Product (IMP) or Investigational product (IP) or therapeutic composition or composition" all means a composition comprising mainly of bone marrow derived allogenic Mesenchymal stem cells along with Human Serum Albumin, PLASMA-LYTE A®, and Dimethyl sulfoxide (DMSO). Hereinafter in the specification it will be referred to as IMP.

In an embodiment, the instant disclosure provides for a composition comprising mainly of Mesenchymal stem cells as active component, Human Serum Albumin, PLASMA-LYTE A® and Dimethyl sulfoxide (DMSO) and a method to obtain the same. The Mesenchymal stem cells are derived from Bone Marrow aspirated from multiple healthy donors preferably 1 to 5 donors, more preferably 1 to 3 donors; and are subjected to various treatments for the preparation of Master cell banks. Further, working cell banks are obtained from said Master cell banks, which are thereafter formulated into the instant composition/(IMP) for therapeutic/clinical application.

Isolation of MSC, Preparation of Master Cell Bank, Working Cell Bank and Investigational Product MCB Preparation:

In an embodiment of the present disclosure, about 60-70 mL of bone marrow is aspirated aseptically from the iliac crest of each healthy donor and is collected into individual blood bags. 20 ml syringe is used to transfer the sample through the cell strainer (100 μm) to remove bone spicules, blood clots and cell aggregates and collected into a centrifuge tube. The bone marrow collected is diluted with complete culture media and the centrifugation is performed at about 1200 rpm to 1500 rpm for about 10 to 20 minutes. The complete culture media comprises, Knockout Dulbecco's Modified Eagle Medium (DMEM-KO), Fetal Bovine Serum (10%), Glutamine (1%) and Pen-Strep [Pencillin-Streptomycin] (0.5%). Discard the supernatant and dilute the pellet with complete culture media. In another centrifuge tube lymphoprep [density gradient solution] is taken and to this double the volume of diluted bone marrow is added and centrifuge at about 1200 rpm to 1500 rpm for about 10 minutes to 20 minutes at room temperature, wherein the room temperature is 20° C. to 25° C. The buffy layer present at the interface is collected and the cells count is performed.

In another embodiment of the present disclosure, the buffy coat comprises of Mononuclear cells (MNCs). MNCs present in buffy coat are washed with complete culture medium. MNC count obtained from each donor is variable, depending upon the age and biological nature of the donor. The average count is about 400-1000 millions. The remaining MNCs are frozen into one vial with count mentioned on the vial. Add equal volumes of the complete culture media to the rest of buffy layer and centrifuge at about 1200 rpm to 1500 rpm for about 10 to 20 minutes. Add culture media to the pellet and gently resuspend. The cells are counted on haemocytometer and about 40-50 Million MNCs are seeded per T-75 flask; and transferred to a 5% $CO_2$ incubator at 37° C. First Media change is done at about 72 hr, thereafter every 48 hr until flasks gets 80%-85% confluency. The media change will ensure that only the MSCs are attached to the surface because of the unique plastic adherence property. After about 48 hours to about 72 hours the cells are screened under microscope and two representative microphotographs are taken.

In an embodiment of the present disclosure, the cells are cultured in the flasks till they attain about 80% to 85% confluency. When the cells are about 80%-85% confluent, aspirate out the complete media and wash the cells twice with Dulbecco's Phosphate Buffer Saline (DPBS). Add about 1-2 ml of trypsin per T-75 flask and incubate at 37° C. for about 2 minutes to 3 minutes. The action of trypsin is neutralized with neutralization media comprising DMEM KO, 10% FBS and 0.5% Pen-Strep [Pencillin-Streptomycin] and the neutralized sample is collected and centrifuge at about 1200 rpm to 1500 rpm for about 10 minutes to 20 minutes at room temperature. To the pellet add complete media, followed by cell counting. Thereafter, freeze MSCs in vials at concentration of about 1 million per ml using the freezing media comprising of about 85% to 95% FBS and about 5% to 15% DMSO, this is referred as Passage 0 (P0) Cells (i.e. 1-2 vials). The rest of the cells are cultured/expanded in cell stacks at a seeding density of about 6,666 cells per sq.cm with complete media change on $7^{th}$ or $8^{th}$ day (culture age) and harvesting the cell stacks by using 0.25% trypsin between 14 to 18th day. Trypsinized cells are neutralized with neutralization media comprising DMEM KO, 10% FBS, 0.5% Pen-Strep [Pencillin-Streptomycin] and collected in a centrifugation tube for centrifugation at about 1200 rpm to 1500 rpm for about 10 minutes to 20 minutes. Pellet is resuspended in complete media to assess cell count. Freeze harvested cells in vials at a concentration of about 1 million cells to 3 million cells per ml in the freezing media comprising of about 85% to 95% FBS and about 5% to 15% DMSO this is referred as Passage 1 (P1) cells or Master Cell Bank.

WCB Preparation:

In another embodiment of the disclosure, one (1) vial each of Master cell bank is taken, the cells are then counted and pooled in equal proposition of each donor. This is referred to as pooling. Pooling can be of 2, 3, 4, 5, or more donors or as per the requirement. After counting and pooling of all donor cells, cells are checked for viability; and viable cell are plated into 2-10 chambers as per the cell counts obtained. Thereafter transfer the culture chambers to a 5% $CO_2$ incubator at about 37° C. After every 48-72 hours observe the cell stacks under microscope and take two representative microphotographs. Replenish the complete culture medium every 7th to 8th day with the freshly prepared complete media comprising DMEM-KO, FBS, Glutamine, Pen-Strep and basic Fibroblast growth Factor (bFGF). The cells are cultured until the cells in the chambers are about 80%-85% confluent.

In an embodiment of the present disclosure, when the cells attain about 80% to 85% confluency, the complete media is aspirated out and the cell stacks are washed twice with DPBS. After washing trypsin is added, and the cells are incubated at about 37° C. for about 4 minutes to 5 minutes, thereafter neutralize them with neutralization media. The neutralized sample is collected and centrifuged at about 1200 rpm to 1500 rpm for about 10 minutes to 20 minutes at room temperature. To the pellet hence obtained, complete media is added and the cells counted. Thereafter culture/expand the cells in the cell stacks for another passage, harvest the cells and centrifuge. To the pellet obtained, complete media is added and the cells are counted. The vials are frozen at about 180° C. to 196° C., such that each vial contains about 1-3 million MSCs in freezing mix comprising about 85% to 95% FBS and about 5% to 15% DMSO. This forms the Working cell bank at Passage 3 (P3). The cryo storage tank used in the instant disclosure makes use of liquid nitrogen and the Working Cell bank is used for future large scale expansion.

Seed Preparation for Large Scale Expansion:

In an embodiment of the present disclosure, depending on the number of cells required for IMP formulation, the specific number of WBC vials are revived and counted. The cell viability is initially checked and the viable cells are plated at a seeding density of about 1000 cells per square centimeter. Thereafter, the vials are transferred to culture chambers and to 5% CO2 incubator, maintained at about 37° C. After every 48 hrs to 72 hrs, the cell stacks are screened under the microscope and two representative microphotographs are taken. The complete medium is then replenished and continued to be replenished after 7 to 8 days with freshly prepared complete media. The cells are then cultured until the chambers are about 80% to 85% confluent.

In another embodiment of the present disclosure, when the cells attain about 80% to 85% confluency, the spent media is aspirated out and the cell stacks are washed twice with DPBS. After washing trypsin is added, incubated at about 37° C. for about 4 minutes to 5 minutes and neutralize with neutralization media. Collect the neutralized sample and centrifuge at about 1200 rpm to 1500 rpm for about 10 minutes to 20 minutes at room temperature ranging from about 20° C. to 25° C. To the pellet add DPBS mix well and centrifuge at about 1200 rpm to 1500 rpm for about 10 minutes to 20 minutes. Resuspend the cells in complete media to access seed cell count. The above drawn cells are referred as Seed Cells at Passage 4 (P4) stage.

Large Scale Production:

In an embodiment of the present disclosure, the above counted viable cells are further actively expanded into multiples of Ten Cell stacks (TCS) (usually 22.4 TCS) at a seeding density of about 1000 to 1100 cells per sq cm. Thereafter, transfer the culture chambers to a 5% $CO_2$ incubator.

In an embodiment of the present disclosure, after every 48-72 hrs screen the cell stacks under microscope and take two representative microphotographs. Addition of about 500 ml of complete media with bFGF to the existing ten cell stacks without removing any spent media on $7^{th}$ or $8^{th}$ day will be referred as Fed batch activation process.

In another embodiment of the present disclosure, replenish the media by Fed batch activation on $7^{th}$ or $8^{th}$ day (culture age) and harvesting the cell stacks by using 0.25% trypsin between 14 to 18 th day. Culture the cells until the chambers are about 80% to –85% confluent.

In yet another embodiment of the present disclosure, when the cells are about 80% to 85% confluent, collect the spent media from the cell stack in a separate centrifuge tube and wash the cell stacks twice with DPBS. After washing add trypsin, and incubate at about 37.degree.C. for about 3 minutes to 4 minutes, neutralize with collected spent media. Collect the neutralized sample in centrifuge tubes and centrifuge at about 1200 rpm to 1500 rpm for about 10 minutes to 20 minutes at room temperature. Resuspend the cells in DPBS and wash twice by centrifugation at about 1200 rpm to 1500 rpm for 10 minutes to 20 minutes. Count the cells under haemocytometer before the final DPBS wash. To the final washed pellet, add freezing mix comprising of PLASMA-LYTE A®, DMSO and Human Serum Albumin and transfer the entire contents to a cryobag. This is the final IMP/composition of the instant disclosure, comprising Mesenchymal stem cells, PLASMA-LYTE A®, Human Serum Albumin (HSA) and DMSO, this can be used for therapeutic/clinical application.

In an embodiment of the present disclosure, the process involved in obtaining the stem cells from the Bone Marrow is provided below:

The present disclosure is further elaborated by the following examples and figures. However, these examples should not be construed to limit the scope of the disclosure.

Example 1

Step 1

Isolation of Bone Marrow Derived MSCs for Master Cell Bank Preparation

1. Pass the bone marrow aspirate through the cell strainer (100 μm) to centrifuge tubes to remove bone spicules and cell aggregates.

2. Dilute the bone marrow with complete culture media in 1:1 ratio comprising Dulbecco's Modified Eagle's Medium Knock-Out [DMEM-KO], Fetal Bovine Serum (FBS), Glutamine and Pen-Strep followed by gentle mixing.
3. Centrifuge at about 1200 rpm to 1500 rpm for about 10 minutes to 20 minutes.
4. Carefully aspirate out the supernatant and dilute the pellet with the complete culture media.
5. In a 50 ml centrifuge tube, lymphoprep is taken and to this double the volume of diluted bone marrow is added (1:2 ratio).
6. Overlay the bone marrow sample onto the lymphoprep carefully so that there is no mixing of sample with lymphoprep.
7. Centrifuge at about 1200 rpm to 1500 rpm for about 10 minutes to 20 minutes at room temperature.
8. To recover Mononuclear cells from the buffy layer which is present in between RBC and plasma rich layer, carefully aspirate the buffy layer by placing the pipette on the corner of the buffy layer at an angle of 45° ensuring not to aspirate any other layers.
9. Transfer the cells to a fresh centrifuge tube and count the cells on haemocytometer
10. Freeze 10 vials of Mononuclear cells (MNC's), each vial containing about 10 million cells.
11. To the rest of buffy layer add equal volumes of the complete culture media and centrifuge at about 1200 rpm to 1500 rpm for about 10 minutes to 20 minutes.
12. Add about 10 ml of the culture media to the pellet and gently resuspend.
13. Count the cells on haemocytometer.
14. Transfer about 40 to about 50 Million MNCs cells to T-75 flask.
15. Transfer the culture chambers to a 5% $CO_2$ incubator at 37° C., and incubate for about 10-15 days.
16. After about 48 hours to about 72 hours observe the cell stacks under microscope and take two representative microphotographs.
17. Replenish the complete medium after the completion of 72 hours and subsequently after the completion of every 48 hours with the freshly prepared complete media.
18. The cells are cultured until the cells in the chambers are about 80% to 85% confluent.
19. When the cells are about 80% to 85% confluent, aspirate out the complete culture media and wash the cell stacks twice with Dulbecco's Phosphate Buffer Saline (DPBS).
20. After washing add about 2 ml of 0.25% trypsin per flask and incubate in a 37° C. incubator for about 2-3 minutes.
21. Neutralize the action of trypsin with neutralization media in the ratio 1:4.
22. Collect the neutralized sample in centrifuge tubes and centrifuge at about 1200-1500 rpm for about 10 minutes-20 minutes at room temperature.
23. To the pellet add complete media and count the cells.
24. Freeze 3-10 vials of previous passage in freezing media comprising of 85% to 95% FBS and 5% to 15% DMSO to a final concentration of 1 million cells to 3 million cells per ml. Expand the culture in 1 Cell Stack (CS) or 2CS at a seeding density of 6666 cells/cm2 to get MCB.
25. Harvest the culture by trypsinization, resuspend the cell pellet in freezing media comprising of about 85% to 95% FBS and 5% to 15% DMSO to a final cell concentration of about 1 million cells to 3 million cells per ml.

Step 2

Preparation of Working Cell Banks from Master Cell Bank

26. Take one (1) vial each of Master cell bank vials from each of the multiple donors.
27. Thaw the vials at about 37° C. in a water bath.
28. Revive the cells by neutralizing the freezing media with complete media in 1:9 ratios.
29. Centrifuge the neutralized suspension at about 1200 rpm to 1500 rpm for 10 minutes to 20 minutes at room temperature.
30. Discard the supernatant and resuspend the pellet with complete media and count the total viable cells of each donor individually.
31. Mix the cells in equal proposition from all donors. This is referred to as pooling. Pooling can be of 2, 3, 4, 5, or more donors.
32. After counting and mixing of all 1-5 or more donor cells check the viability and plate viable cells with a seeding density of about 1000 cells/cm$^2$ in 2 chambers and 10 chambers as per the cell counts obtained.
33. Thereafter transfer the culture chambers to a 5% $CO_2$ incubator at about 37° C.
34. After every 48 to 72 hours screen the cell stacks under microscope and take two representative microphotographs.
35. Replenish the complete medium every 7th to 8th day with the freshly prepared complete media comprising DMEM-KO, FBS, Glutamine, Pen-Strep and bFGF.
36. Then culture the cells until the cells in the chambers are about 80% to 85% confluent.
37. When the cells are about 80% to 85% confluent, aspirate out the complete media and wash the cell stacks twice with DPBS.
38. After washing add about 0.25% trypsin of 20 ml per chamber, and incubate in a 37° C., for about 4 to 5 minutes.
39. Neutralize the action of trypsin with complete media in the ratio 1:4
40. Collect the neutralized sample in centrifuge tubes and centrifuge at about 1200 rpm to 1500 rpm for about 10 minutes to 20 minutes at room temperature.
41. To the pellet add about 10 ml to 20 ml of the complete media and count the cells.
42. Expand the cells in the cell stacks for another passage and harvest the cells as per steps 37-41.
43. Centrifuge the cells at about 1200 rpm to 1500 rpm for about 10 minutes to 20 minutes at room temperature, discard the supernatant and resuspend the pellet with freezing media consisting of about 5% to 15% DMSO and about 85% to 95% FBS.
44. Mix gently and fill the cryo vial containing 1 Million cells/ml to 3 Million cells/ml of freezing media and labeled as WCB at Passage 3 (P3).

Step 3

Preparation of Composition from Working Cell Bank Vials

45. Revive required number of vials of working cell bank depending on IMP requirement, count cells and check their viability. Plate about 6.36 million viable cells/10 chamber cell stack.

46. Transfer the culture chambers to a 5% CO2 incubator at about 37.degree.C.
47. After every 48 hours to 72 hrs observe the cell stacks under microscope and take two representative microphotographs.
48. Replenish the complete medium every 7th day to 8th day with the freshly prepared complete media.
49. Culture the cells until the chambers are about 80% to 85% confluent.
50. When the cells are about 80% to 85% confluent, aspirate out the spent media and wash the cell stacks twice with DPBS.
51. After washing add about 20 ml of 0.25% trypsin per chamber, and incubate in a 37.degree.C. incubator for about 2 minutes to about 3 minutes.
52. Neutralize the action of trypsin with complete media in the ratio 1:4.
53. Collect the neutralized sample in centrifuge tubes and centrifuge at about 1200 rpm to 1500 rpm for about 10 minutes to 20 minutes at room temperature.
54. To the pellet add about 20 ml of DPBS mix well and centrifuge at about 1200 rpm to 1500 rpm for 10 minutes to 20 about minutes.
55. Resuspend the cells in complete media measure cell count. The above drawn cells are referred as Seed Cells at P4 stage.
56. Seed the P4 cells for one more expansion in multiples of Ten Cell stacks (usually 22.4 TCS) at a seeding density of about 1000 to 1100 cells per sq cm. Transfer the culture chambers to a 5% CO2 incubator.
57. After every 48-72 hrs screen the cell stacks under microscope and take two representative microphotographs.
58. Add about 500 ml complete media with bFGF to the ten cell stacks without removing any spent media on 7.sup.th or 8.sup.th day.
59. Harvest the cell stacks by using 0.25% trypsin between 14 to 18th day when chambers are about 80% to 85% confluent.
60. When the cells are about 80% to 85% confluent, collect the spent media form the cell stack in a separate centrifuge tube and wash the cell stacks twice with DPBS.
61. Add trypsin, and incubate in a 37.degree.C. incubator for about 3 minutes to 4 minutes, neutralize with collected spent media.
62. Collect the neutralized sample in centrifuge tubes and centrifuge at about 1200 rpm to 1500 rpm for about 10 minutes to 20 minutes at room temperature.
63. Resuspend the cells in DPBS and wash twice by centrifugation at about 1200 rpm to 1500 rpm for 10 minutes to 20 minutes.
64. Count the cells under haemocytometer before the final DPBS wash.
65. To the final wash pellet add about 15 ml of freezing mix comprising about 12.75 ml of PLASMA-LYTE A®, about 1.5 ml of DMSO and about 0.75 ml of Human Serum Albumin, for about 200 million cell pellet. Transfer the entire contents to a cryobag. This is the final composition of the instant disclosure, comprising Mesenchymal stem cells, PLASMA-LYTE A®, Human Serum Albumin and DMSO, this can be used for therapeutic/clinical application.

In an embodiment of the present disclosure, the Mesenchymal Stem cells in the Master Cell Bank composition comprises of about 1 million cells and in Working Cell Bank composition comprises of about 3 million cells in each vial.

Example 2

Establishing Master Cells Bank

FIG. 1 shows major steps involved in the in preparation of Master cell bank (MCB) from isolated bone marrow. Step 101 is selection of healthy donor of age group 19-35, step 103 aspiration of bone marrow from the selected donor screened for human immunodeficiency virus (HIV1), hepatitis B (HBV), hepatitis C(HCV) and cytomegalovirus (CMV) as a mandatory screening test. Bone marrow (60-80 mL) is aseptically aspirated from the iliac crest of multiple donors under general anesthesia. Step 105 is plating/seeding of Mononuclear cells (MNC) followed by harvesting MSC of Passage 0 (P0) 107 and reseeding MSC from P0 109. Step 111 consists of harvesting of MSC at Passage 1 (P1) to establish Master cells bank (MCB). Cryopreservation 113 of MCB (1 Million cells/ml to 3 Million cells/mL), in cryopreservation solution comprising of about 85% to 95% FBS and about 5-15% DMSO.

Establishing Working Cell Bank

Figure 2:
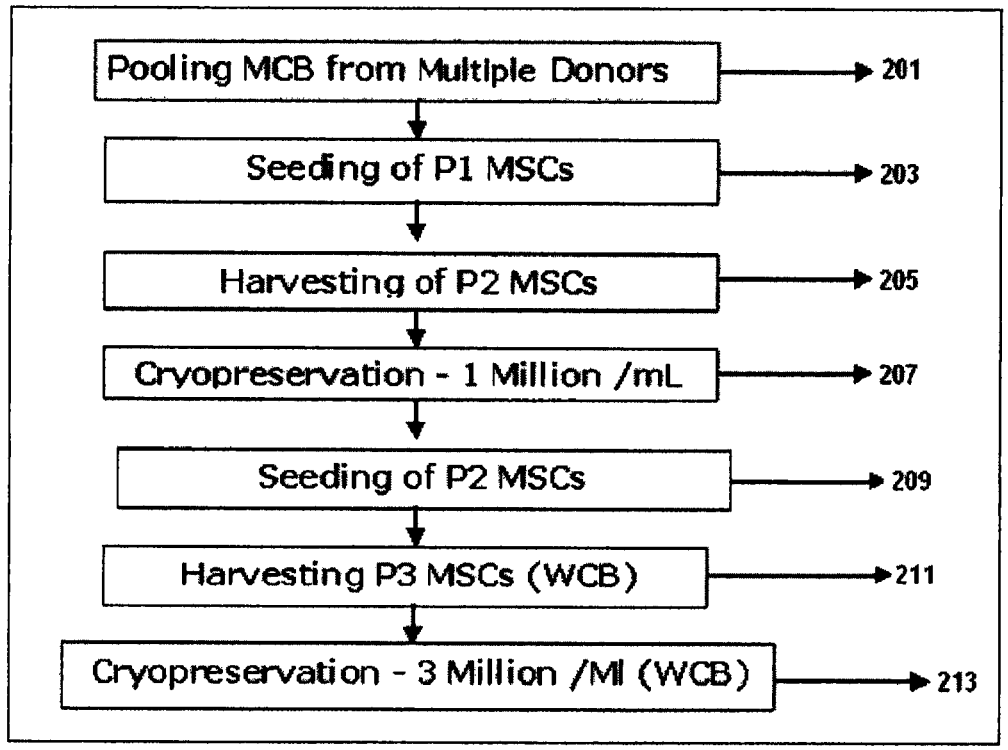
FIG. 2 shows a flow chart depicting steps involved in arriving at Working Cell Bank (WCB).

FIG. 2 illustrates major steps involved in preparation of working cell bank (WCB) from Master cell bank (MCB). Step 201—pooling of MCB from multiple donors, 203—seeding of P1 MSCs, 205—harvesting of P2 MSCs, 207—cryopreservation of P2 MSC's, 209—reseeding P2 MSCs, 211—harvesting P3 MSCs which constitute the Working Cell Bank (WCB), 213—comprising of MSCs cryopreserved at aliquots of 1-3 million cell/ml in a cryopreservation mix/freezing mix comprising of about 85% to 95% FBS and about 5% to 15% DMSO.

Figure 3:
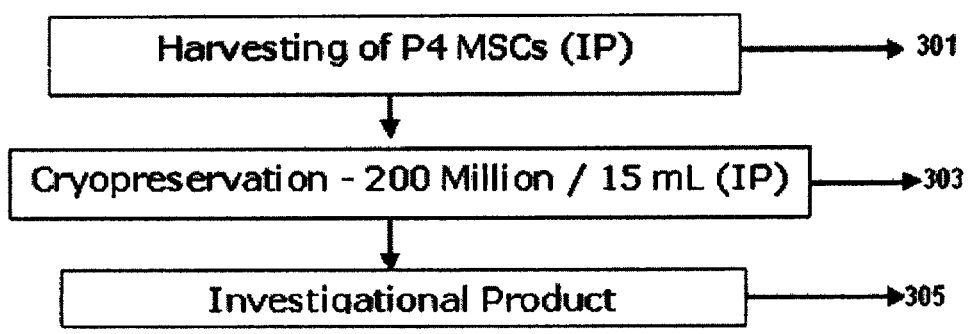
FIG. 3 shows a flow chart depicting steps involved in arriving at final composition/Investigational product (IP)/Investigational Medicinal Product (IMP).
Figure 4:
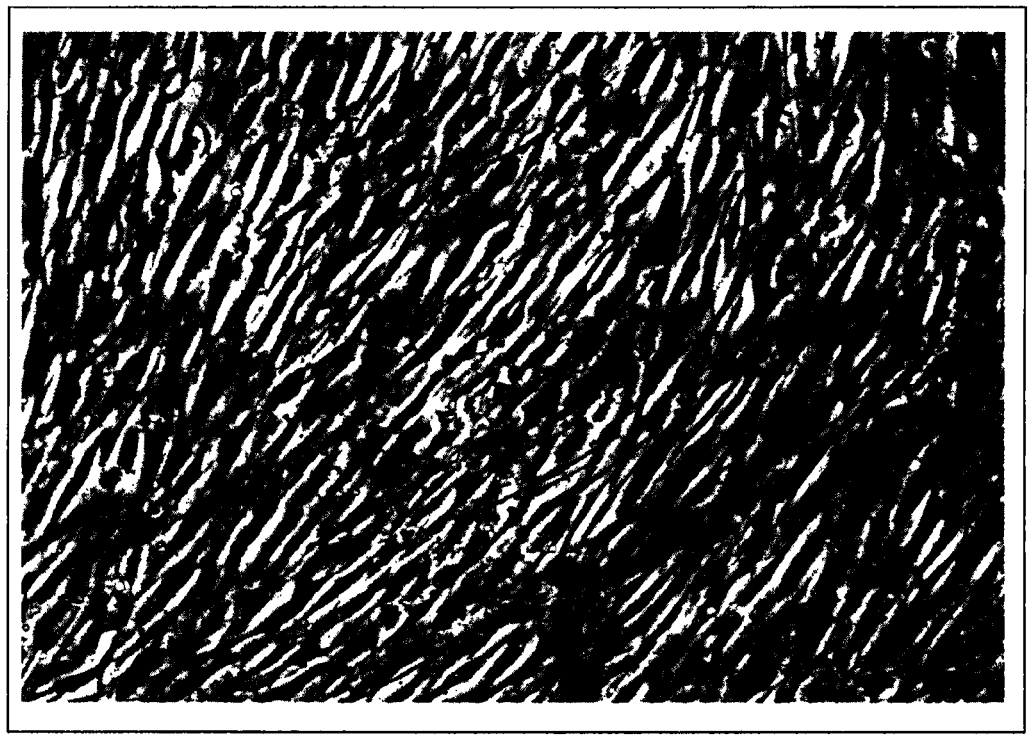

Formulating Investigational Product (IP)/Investigational Medicinal Product (IMP)/Therapeutic Compositions FIG. 3 illustrate various important steps carried out to formulate a therapeutic compositions also referred to as Investigational Product (IP)/Investigational Medicinal Product (IMP) for this application. The IP comprises mainly of bone marrow derived allogenic Mesenchymal Stem Cells (MSC) with other minor component. The required number of bags with defined quantity of cells from P3 is revived and seeded into complete culture media to harvest Passage 4 (P4) cells 301, which form the IP. This can be further cryopreserved 303 in freezing mix/cryopreservation mix comprising of PLASMA-LYTE A®, DMSO and Human Serum Albumin (HSA). The final Investigational Product 305 comprises 200 million cells, 12.75 ml PLASMA-LYTE A®, 1.5 ml DMSO and 0.75 ml Human Serum Albumin (HSA).

In one of the embodiment the IMP comprises Mesenchymal Stem Cells having concentration ranging from about 25 million to about 200 million cells; the Human Serum Albumin having concentration ranging from about 1% to about 6%; the PLASMA-LYTE A®, having concentration ranging from about 80% to about 90%; the Dimethyl Sulfoxide having concentration ranging from about 5% to about 10%.

Example 3

In one embodiment three healthy donors (A, B & C) are selected in the age group 19-35 years. The patients are screened for human immunodeficiency virus (HIV1), hepatitis B (HBV), hepatitis C(HCV) and cytomegalovirus (CMV) as a mandatory screening test. Bone marrow (60-80 mL) is aseptically aspirated from the iliac crest of three donors under deep sedation considering the quantity of MSCs in Bone Marrow is 0.01 to 0.001% (Pittenger 1999), the quantity of MSCs obtained from a quantity below the range will be too low to proceed and above the range may give rise to unwanted components such as RBCs.

TABLE 1

| Donor Code: | Donor A | Donor B | Donor C |
|---|---|---|---|
| Donor screening and Bone Marrow Aspiration: | | | |
| Age (Year) | 20 | 22 | 19 |
| Body Weight (Kg) | 53 | 68 | 64 |
| Quantity of BM Collected | 60 mL | 60 mL | 60 mL |
| Isolation of Mononuclear Cells | | | |
| Buffy coat | 58 mL | 55 mL | 60 mL |
| MNC (Millions) | 400 | 450 | 800 |

The bone marrow aspirate is collected in 4-5 centrifuge tubes by passing through 100 um (pore size) cell stainer to remove any bone spicules and blood clots and is diluted with complete culture medium in (1:1) ratio. The completed culture medium comprises of Knockout Dulbecco's Modified Eagle Medium (DMEM-KO) supplemented with Fetal Bovine serum (FBS), Glutamine and Pen-Strep. The bone marrow aspirate is centrifuged at about 1200 rpm to 1500 rpm. for about 10 minutes to 20 minutes to remove plasma. The supernatant is discarded and the resuspended pellet is layered onto a Lymphoprep in 2:1 ratio (suspended BMA: lymphoprep). Mononuclear cells (MNCs) are derived from the buffy coat of Lymphoprep density gradient obtained after centrifugation of about 1200 rpm to 1500 rpm for about 10 minutes to 20 minutes. The MNCs present in the buffy coat are washed again with complete culture medium. MNC count obtained from each donor is variable, depending upon the age and biological nature of the donor. The average count is about 400 to 1000 millions.

Example 4

Passage of MNCs to Get MSCs (P0)

The mononuclear fraction, which also contains MSCs, is plated onto T-75 flasks (BD Biosciences) and cultured in complete culture media comprising of DMEM-KO supplemented with 10% FBS, 200 mM GLUTAMAX™ (glutamine dipeptide) and Pen-Strep, Optimal seeding density is about 40-50 million per T-75 flask. First media change shall be performed after 72 hours of incubation and subsequent media changes after every 48 hours, till a confluency level of about 80%-85% is obtained. A maximum of 5 media changes are performed to ensure the sufficient proliferation of cells and removal of non adherent cells. However, the number of media changes may vary based upon the confluency of cells. Once the cells become confluent, they are dissociated with 0.25% trypsin/0.53 mM EDTA (Invitrogen) and reseeded at the rate of 6666 cells/cm2 (passage 1). After 3-5 days of culture, the cells reach about 80% to 85% confluency and are harvested in order to freeze 1 million cells to 3 million cells per ml as MCB. Table 2 shows the details of isolation of MSC at P0.

TABLE 2

Isolation of Mesenchymal Stem Cells (P0):

| | Donor | | |
|---|---|---|---|
| | Donor A | Donor B | Donor C |
| Seeding Density | 40-50 million per T-75 | 40-50 million per T-75 | 40-50 million per T-75 |
| Qty. of complete media added per T-75 flask | 75 ml | 75 ml | 75 ml |

TABLE 2-continued

Isolation of Mesenchymal Stem Cells (P0):

| | Donor | | |
|---|---|---|---|
| | Donor A | Donor B | Donor C |
| Incubation condition | 36.9° C.-37° C. | 36.9° C.-37° C. | 36.9° C.-37° C. |
| Media Change - 1 on | 72 hr | 72 hr | 72 hr |
| Subsequent 4 -Media Change - | every 48 hr | every 48 hr | every 48 hr |
| Total time taken for passage P0 | 9-13 days | 9-13 days | 9-13 days |
| Confluency % at harvest | 80-90% | 80-90% | 80-90% |
| Total Cell Count | 75 Millions | 74 millions | 50 millions |

Example 5

Passage (P1)-MCB

Multiple of one or two cell stacks is found to be the optimal one for expansion at this stage. Usage of multiple of 1 or 2 cell stack is more beneficial with respect to 5-10 cell stack, in terms of yield and cell stack shall be viewed under microscope to monitor the confluency of cells during incubation. Seeding density of 6666 cell/cm$^2$ is found to be optimal. Incubation period is about 6-9 days from the day of seeding, at 37° C. and 5% $CO_2$. Each individual donor is to be processed in the same manner to get the P1 of uniform cell count and shall frozen in 1 million per vial and stored at about 180° C. to 196° C. The above frozen P1-MCB vials are randomly selected for QC testing. The thawed MCB should have >85% viability and >80% of these cells should be positive for MSC surface markers (indication of Purity) and <5% for negative marker. Table 3 provides the overview of Passage 1 (P1).

TABLE 3

Passage 1 (P1): MCB

| | Donor | | |
|---|---|---|---|
| | Donor A | Donor B | Donor C |
| Cell Stack Used | Multiple of One or two CS | Multiple of One or two CS | Multiple of One or two CS |
| Seeding Density | 6666 cell/cm2 | 6666 cell/cm2 | 6666 cell/cm2 |
| Qty. of complete media added per 1 CS | 150 ml | 150 ml | 150 ml |
| Incubation condition | 36.9° C.-37° C. | 36.9° C.-37° C. | 36.9° C.-37° C. |
| Confluency % | 70-80% | 70-80% | 70-80% |
| Viability tested by Flow cytometry | >85% | >85% | >80% |
| Total time taken for passage P1 | 6-9 days | 6-9 days | 6-9 days |
| Cell Count | 120 millions | 74 millions | 110 millions |

Example 6

Passage (P2)

Mixing of individual donors is required to provide homogenous product, which in turn is required to reduce the rejection from the recipient. To this affect P1 vials of three donors of equal proportion are mixed and plated into one or two cell stacks at a seeding density of 1000 cell/cm² in bFGF enriched complete media Media change on 7-8$^{th}$ day and incubation period is 14-18 days from the day of seeding, at 37° C. and 5% $CO_2$. The thawed MCB should have >85% viability and >80% of these cells should be positive for MSC surface markers (indication of Purity) and <5% for negative marker.

Example 7

Passage (P3)

The above active cells are further sub-cultured in ten cell stacks and two cell stacks as control at 1 at a seeding density of 1000 cell/cm² in bFGF enriched complete media. Media change on 7-8$^{th}$ day and incubation period is 14-18 days from the day of seeding, at 37° C. and 5% $CO_2$, P3 is a replica of P2 in all aspects, except the number of vials produced out of it. All parameters applicable to P2 are applicable for P3 also. This shall be frozen in multiple of vials and each of 1-3 million per vial. These are used as WCB-P3 cells.

Example 8

Passage (P4)-Seed 2-3 vials of WCB are taken and plated into multiple one or two cell stack as seed preparation for large scale IMP preparation. These cells are seeded and harvested in the same method as that of P3.

Example 9

Passage (P5)-IMP Preparation

The above active cells are further sub-cultured in multiple of ten cell stacks and two cell stacks as control at 1 at a seeding density of 1000 cell/cm² in bFGF enriched complete media. Media change on 7-8$^{th}$ day and incubation period is 14-18 days from the day of seeding at 37° C. and 5% $CO_2$ Harvested cells are frozen in multiples of cryobags (each of 25 million cells to 200 million cells) in formulation media. The thawed MCB should have >85% viability and >80% of these cells should be positive for MSC surface markers (indication of Purity) and <5% for negative marker. This is used for clinical application as therapeutic composition/investigational product IP)/Investigational Medicinal Product (IMP). Table 4 below show the different stages involved in obtaining IP.

TABLE 4

| Passage | Stage to obtain IP | Remarks |
|---|---|---|
| P0 | | NA |
| P1 | Master Cell Bank | For individual donors. |
| P2 | | Mixed population of donors, used for generation of Working Cell Bank (WBC). |
| P3 | Working Cell Bank | Replica of P2 and used for further passage. |
| P4 | Seed for IMP | Replica of P3 interms of Seeding and expansion |
| P5 | Investigational Medicinal Product | Used for clinical application. |

Example 10

Characterization Studies

Allogenic MSCs of the instant disclosure is a multiple donor derived ex vivo culture of adult human mesenchymal stem cells. It consists of homogeneous population of mesenchymal stem cells characterized for specific cell markers such as cell surface phenotype. Mesenchymal stem cells of the instant disclosure are analyzed by flow cytometry using CD 14, CD 19, CD 34, CD 45, CD 73, CD 90, CD 105, CD 133, CD 166, and HLA-DR markers. The MSCs of the instant disclosure's composition are more than 80% positive for CD 73, CD 90 CD105, and CD 166 but less than 10% positive for CD14, CD19, CD 34 CD 45, CD 133 and HLA-DR. Table 5 below show the of CD marker comparison for different batches of IMP at passage 5 obtained by the method disclosed in the application using Flow cytometery.

Comparison of CD Markers for 3 Donor IMP (P5)

TABLE 5

| PURITY (FLOW CYTOMETERY) | SPECIFICATION | DSM-IP-0109 A1 | DSM-IP-0109 A2 | DSM-IP-0109 A3 | DSM-IP-0109 A4 | DSM-IP-0109 A6* | DSM-IP-0109 A7 |
|---|---|---|---|---|---|---|---|
| CD166 | >80% | 97.00% | 99.36% | 96.18% | 99.66% | 98.38% | 97.74% |
| CD73 | >80% | 92.70% | 99.50% | 95.35% | 99.92% | 99.04% | 99.48% |
| CD105 | >80% | Not Done | Not Done | Not Done | Not Done | 94.78% | Not Done |
| CD90 | >80% | 87.80% | 95.35% | 95.35% | 94.86% | 99.04% | 91.58% |
| CD34 | <5% | 0.56% | 0.14% | 0.12% | 0.22% | 0.46% | 0.24% |
| CD45 | <5% | 0.74% | 0.00% | 1.24% | 0.02% | 0.06% | 0.22% |
| CD133 | <5% | 0.04% | 1.24% | 0.32% | Not done | 2.84% | 0.58% |
| HLADR | <5% | 0.62% | 0.78% | 0.70% | 0.02% | 0.18% | 2.88% |

In an embodiment of the present disclosure, the kit comprises the present disclosure's composition, the Master cell or Working cell Bank composition and the instructions manual to prepare the compositions. The composition comprises Mesenchymal Stem Cells, Human Serum Albumin (HSA), PLASMA-LYTE A® and Dimethyl Sulphoxide (DMSO), optionally along with pharmaceutically acceptable additives. Further, the Master cell or Working cell Bank Composition comprising Mesenchymal stem cells, Fetal Bovine Serum (FBS) and Dimethyl Sulphoxide (DMSO).

We claim:

1. A method of preparing a composition comprising Mesenchymal stem cells, Multiple Electrolytes Injection, Type I USP, Human Serum Albumin (HSA), Dimethyl Sulphoxide (DMSO), optionally along with pharmaceutically acceptable additives, comprising the steps of, in sequential order:
   a) preparing a Working Cell Bank composition by pooling mesenchymal stem cells from multiple master cell bank compositions, wherein each master cell bank composition is obtained from bone marrow cells of a single donor, said master cell bank composition comprising mesenchymal stem cells, Fetal Bovine Serum (FBS) and DMSO, said preparation comprising acts of:
      i) thawing mesenchymal stem cells from the master cell bank compositions, reviving the cells by neutralizing with culture media to obtain a neutralized cell suspension and centrifuging the neutralized cell suspension;
      ii) suspending the cell pellet from each master cell bank composition in the culture media and pooling the cells from each of the master cell bank compositions in equal proportions to obtain pooled cells;
      iii) harvesting the pooled cells, centrifuging the harvested cells and freezing in freezing media to obtain the working cell bank composition comprising pooled mesenchymal stem cells from multiple donors, FBS ranging from about 85% to 95% and DMSO ranging from about 5% to 15%;
   b) obtaining pooled mesenchymal stem cells from the Working Cell Bank composition obtained in a), followed by culturing the cells with culture media to achieve about 80% to 85% confluency;
   c) harvesting the confluent cells by aspirating spent culture media, washing the confluent cells with Dulbecco's Phosphate Buffered Saline (DPBS) and treating the cells with 0.25% trypsin;
   d) neutralizing the trypsin of the treated cells with the culture media and thereafter centrifuging the cells to obtain a cell pellet and suspending the cell pellet in the complete media;
   e) culturing the cells of step (d), in the complete media to achieve about 80% to 85% confluency;
   f) harvesting the confluent cells by washing the cells with the DPBS; treating the washed cells with 0.25% trypsin followed by neutralizing the trypsinized cells with the complete media;
   g) centrifuging the neutralized cell suspension and washing the centrifuged cells with the DPBS followed by re-centrifuging to obtain a pellet; and
   h) freezing the pellet with the Multiple Electrolytes Injection, Type I USP, the DMSO and the Human Serum Albumin; and optionally adding pharmaceutically acceptable additive to obtain the composition.

2. The method of claim 1, wherein the pooled Mesenchymal stem cells of the Working Cell Bank composition ranging from about 1 million cells to 3 million cells.

3. The method of claim 1, wherein the centrifuging is carried out at about 1200 rpm to 1500 rpm, at temperature ranging from about 20° C. to 25° C. for time duration ranging from about 10 minutes to 20 minutes.

4. The method of claim 1, wherein the confluency is obtained by replenishing the culture media after about 7 days to 8 days.

5. The method of claim 1, wherein the culture media comprises Dulbecco's Modified Eagle Medium-KnockOut at a concentration ranging from about 85% to 95%, Fetal Bovine Serum at a concentration ranging from about 5% to 15%, Glutamine at a concentration ranging from about 0.5% to 2%; Pen-Strep at a concentration ranging from about 0.1% to 1%, and basic Fibroblast growth Factor at a concentration ranging from about 0.5 ng/ml to 5 ng/ml.

6. A method of preparing an allogeneic mesenchymal stem cell (MSC) composition, comprising the steps of, in sequential order:
   a) preparing a plurality of Master Cell Banks (MCB), each MCB comprising one container of MSCs from bone marrow cells of a single donor;
   b) pooling in equal proportion, at least 2 or more of the MCBs, wherein each container contains MSCs from a single donor, to obtain a plurality of MSCs from the 2 or more donors;
   c) culturing the pooled MSCs from b) for at least 2 passages to obtain a working cell bank composition (WCB) of pooled mesenchymal stem cells from a plurality of donors;
   d) harvesting and cryopreserving the cells of c) to form an allogeneic pooled MSC composition; and
   e) culturing the cells of d) for at least 1 passage to produce an allogeneic MSC population derived from a plurality of donors and optionally adding a pharmaceutically acceptable additive to the cell composition.

* * * * *